(12) United States Patent
Taneja et al.

(10) Patent No.: US 8,445,700 B2
(45) Date of Patent: May 21, 2013

(54) PROCESS FOR THE PREPARATION OF OPTICALLY ACTIVE N-BENZYL-3 HYDROXYPYRROLIDINES

(75) Inventors: Subhash Chandra Taneja, Jammu Tawi (IN); Mushtaq Ahmad Aga, Jammu Tawi (IN); Brijesh Kumar, Jammu Tawi (IN); Vijay Kumar Sethi, Jammu Tawi (IN); Samar Singh Andotra, Jammu Tawi (IN); Ghulam Nabi Qazi, Jammu Tawi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/130,702

(22) PCT Filed: Nov. 24, 2009

(86) PCT No.: PCT/IN2009/000680
§ 371 (c)(1),
(2), (4) Date: Jan. 10, 2012

(87) PCT Pub. No.: WO2010/058429
PCT Pub. Date: May 27, 2010

(65) Prior Publication Data
US 2012/0101285 A1  Apr. 26, 2012

(30) Foreign Application Priority Data
Nov. 24, 2008 (IN) .......................... 2648/DEL/2008

(51) Int. Cl.
*C07D 207/12* (2006.01)
*C07D 471/02* (2006.01)

(52) U.S. Cl.
USPC .......................................... 548/541; 544/252

(58) Field of Classification Search
USPC .......................................... 548/541; 544/252
See application file for complete search history.

(56) References Cited

U.S. PATENT DOCUMENTS

| 4,916,141 | A | 4/1990 | Sanchez |
| 5,109,008 | A | 4/1992 | Scopes et al. |
| 5,187,094 | A | 2/1993 | Sawa et al. |
| 5,233,053 | A | 8/1993 | Cross et al. |
| 5,281,711 | A | 1/1994 | Scherschlicht et al. |
| 5,463,064 | A | 10/1995 | Tamazawa et al. |
| 7,141,412 | B2 | 11/2006 | Li et al. |

FOREIGN PATENT DOCUMENTS

| EP | 0304087 A2 | 2/1989 |
| EP | 0330469 A2 | 8/1989 |
| EP | 0431521 A1 | 6/1991 |
| EP | 0452143 A2 | 10/1991 |
| EP | 0483580 A2 | 5/1992 |
| EP | 1002871 A1 | 5/2000 |
| JP | 01-141600 A | 6/1989 |
| JP | 04-131093 A | 5/1992 |
| JP | 04-164066 A | 6/1992 |
| JP | 05-227991 A | 9/1993 |
| JP | 05-279325 A | 10/1993 |
| JP | 05-279326 A | 10/1993 |
| JP | 06-141876 A | 5/1994 |
| WO | 91/09013 A1 | 6/1991 |
| WO | 95/03219 A1 | 2/1995 |
| WO | 95/03421 A1 | 2/1995 |
| WO | 98/23768 A1 | 6/1998 |
| WO | 2007/024113 A1 | 3/2007 |

OTHER PUBLICATIONS

Ibragimov et al. (CAPLUS Abstract of Khimiya Prirodnykh Soedinenii (1989), (1), 18-23).*
Mitsunori Hashimoto, et al; "A Novel Decarboxylation of α-Amino Acids. A Facile Method of Decarboxylation by the Use of 2-Cyclohexen-1-One as a Catalyst", Chemistry Letters, Jun. 1986, No. 6, pp. 893-896.
P. Di Cesare, et al; "Fluoronaphthyridines and quinolones as Antibacterial Agents. 5. Synthesis and Antimicrobial Activity of Chiral 1-*tert*-Butyl-6-fluoro-7-substituted-naphthyridones", Journal of Medicinal Chemistry, American Chemical Society, Washington, US LNKD-DOI: 10.1021/JM00100A028, vol. 35, Jan. 1, 1992, pp. 4205-4213, XP002175569, ISSN: 0022-2623 Scheme II, cp.7→→16.
Akira Horiguchi et al; "Enzymatic Optical Resolution of N-Benzyl-3-Pyrrolidonol", Bioscience Biotechnology Biochemistry, Japan Society for Bioscience, Biotechnology and Agrochemistry, Tokyo, Japan, vol. 59, No. 7, Jul. 1, 1995, pp. 1287-1290, XP002948377 ISSN: 0916-8451 the whole document.
International Search Report: mailed Jun. 5, 2010; Appln. PCT/IN2009/000680.

* cited by examiner

*Primary Examiner* — Robert Havlin
(74) *Attorney, Agent, or Firm* — Ladas & Parry LLP

(57) ABSTRACT

The present invention relates to a facile, highly efficient and economical process for the preparation of optically active N-benzyl-3-hydroxypyrrolidine in high yield from a naturally occurring alkaloid vasicine. The natural alkaloid vasicine is used as a precursor of (S)—N-benzyl-3-hydroxypyrrolidine and (R)—N-benzyl-3-hydroxypyrrolidines which can easily be sourced from the medicinal plant Adatoda vasica by the method known in the art and transformed to optical isomers (R) and (S)—N-benzyl-3-hydroxypyrrolidine by the method described in the present invention.

11 Claims, 1 Drawing Sheet

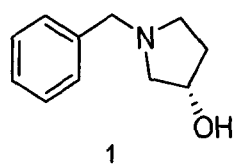
1
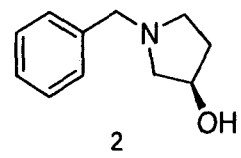
2
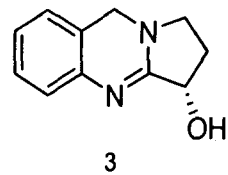
3
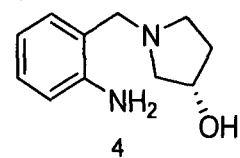
4
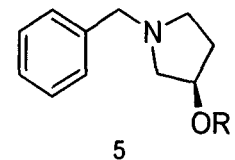
5
R = HCO, CH₃CO, CH₃CH₂CO, CH₃CH₂CH₂CO

PROCESS FOR THE PREPARATION OF OPTICALLY ACTIVE N-BENZYL-3 HYDROXYPYRROLIDINES

FIELD OF THE INVENTION

The present invention relates to a facile and highly efficient process for the preparation of optically active N-benzyl-3-hydroxypyrrolidines starting from naturally occurring alkaloid vasicine. The alkaloid vasicine is an easily available raw material isolated from the plant sources. Optically active N-benzyl-3-hydroxypyrrolidines are useful intermediates for the preparation of several pharmaceutical products, antibiotic drugs and agricultural chemicals. The present invention discloses a novel and efficient process of its synthesis which can be of commercial importance.

BACKGROUND OF THE INVENTION

Optically active 3-hydroxy-N-benzylpyrrolidine and its derivatives are widely used as intermediates of various chiral medicines such as carbapenem antibiotics (panipenem), vasodilation (Barnidipine) or antihypertensive (Darifenacine, Lirequill, Clina floxacine) drugs (EP 483580; EP 330469; EP 304087; U.S. Pat. No. 5,463,064; U.S. Pat. No. 5,281,711; U.S. Pat. No. 5,109,008; U.S. Pat. No. 4,916,141; WO 91/09013). Several compounds are also reported to be clinically tested. Enantiomerically pure 3-hydroxy-N-benzylpyrrolidine is also a useful intermediate for various agrochemicals. Literature methods for preparing enantiomerically pure 3-hydroxy pyrrolidine and its derivatives are as follows.

1) A process for the preparation of 3-hydroxypyrrolidine involves decarboxylation of chiral 4-hydroxy-2-pyrrolidinecarboxylic acid (WO 91/09013; U.S. 5233053, *Chem. Lett.* 1986, 893). This process suffers from low yield and a number of synthetic steps.

2) Hydroboration of N-substituted 3-pyrrolidine with diisopinocomphenyl borane followed by oxidation with alkaline hydrogen peroxide gave enantiomerically pure 3-hydroxypyrrolidine (Brown H. C., et. al *J. Am. Chem. Soc.,* 1986, 108-2049; Brown, H. C., et al, *J. Org. Chem.;* 1986, 51, 4296). The process may not be suitable for industrial production because of the use of special borane reagent.

3) One of the common methods for the preparation of N-substituted 3-hydroxy pyrrolidine is the condensation reaction of natural malic acid with benzylamine and subsequent reduction reaction with a strong reducing agent (*Synth. Commun.* 1983, 13, 117 and *Synth. Commun.* 1985, 15, 587). Optically active N-benzyl-3-hydroxy pyrrolidine was also prepared starting from glutamic acid. The intermediate 3-hydroxypyrrolidinone is reduced by a strong reducing agent to give N-benzyl-3-hydroxypyrrolidine (*Synth. Commun.* 1986, 16, 1815). Although the above methods have the advantages that chiral 3-hydroxypyrrolidine and its derivatives can be produced from commercially available raw materials, however, the reducing agent used in these processes are expensive and the required reaction conditions are not suitable for large scale production.

4) 3-Hydroxy pyrrolidine was also reportedly prepared by reacting 1, 4-dibromo-2-butanol with benzyl amine (*J. Med. Pharm. Chem.,* 1959, 1, 76). Selective bromination at 1, 4 position is not controlled easily, and the yields are low (31%). Moreover, the use of expensive brominating reagents makes the process unsuitable for large scale production.

5) Some classical processes used chemical resolution agents, to obtain optically active 3-hydroxypyrrolidine and its derivatives from racemic mixtures [(JP 05/279326 (1993); JP 05/279325 (1993); JP 04/164066 (1992)]. Again the reported yields are low, and these processes are not efficient for large scale production.

6) Process for resolving racemic 3-hydroxypyrrolidine derivatives using enzymatic resolution via hydrolysis [(WO 95/03421 (1995); U.S. 5187094 (1993); JP 01/141600 (1995)] and esterification [(WO 95/03219 (1995); JP 05/227991 (1993); JP 04/131093 (1992)] lack practicality and the synthesis of racemic starting material is also a drawback.

7) Use of biocatalyst for the preparation of optically active 3-hydroxypyrrolidine, where in an oxygen atom is inserted stereoselectively in the corresponding pyrrolidine nucleus is one of the promising processes, however, low yield, high dilution and low enantiomeric excess of the product are some of the main draw backs (U.S. Pat. No. 7,141,412). Enzymatic hydroxylation of pyrrolidines is complicated. Hydroxylation of N-benzyl-3-hydroxypyrrolidine with *Pseudomonas putida* gave corresponding 3-hydroxypyrrolidine in low yield as well as low enantiomeric excess (EP 1002871). There is also a report of hydroxylation by *Khim. Geterotsikl. Soedin.* using specific fungi, *Cunninghamella verticillate,* or *Aspergillus niger* (Chemical Abstract, 1993, 118: 6835C). It is doubtful whether the method is applicable to the hydroxylation of N-acylpyrrolidines, moreover the process suffers from low yield. The biocatalytic hydroxylation process is perhaps the only process which is being commercially used for the production of the target molecules.

8) Process for preparing enantiomerically pure 3-hydroxy-pyrrolidinone [(JP 06/141876 (1994); WO 98/23768 (1998)] also faces the same difficulties as mentioned above.

9) Recently 3-hydroxypyrrolidine and its N-substituted derivative were prepared by cyclisation of 4-halo-3-hydroxy butane derivatives [(EP 452143 (1991)] e.g. cyclization of enantiomerically pure 4-chloro-3-hydroxy butylnitrile [(EP 431521 (1988)], and 3-chloro-2-hydroxy propionitrile (WO 2007/024113). However, enantiomerically pure starting materials are expensive and not easily available, so the process is not less viable. It is evident that though, there are various methods for the preparation of enantiomerically rich N-benzyl-3-hydroxypyrrolidine and its derivatives documented in the literature, yet an efficient process of preparation of enantiomerically pure product from an inexpensive and easily available raw material is one of the important challenges in the field of synthetic and medicinal industry.

The present process of the preparation of both the enantiomers i.e. (R) and (S)-3-N-benzyl-3-hydroxypyrrolidines with high optical purity from the easily available raw material with its sustainable supply, renewable source, facile reaction methodology and high yields, makes it an attractive and commercially viable method.

SUMMARY OF THE INVENTION

Accordingly the present invention provides a process for the preparation of optically active N-benzyl-3-hydroxypyrrolidine from a natural alkaloid (−)-vasicine comprising the steps:

a. reacting (−)-vasicine of formula 3

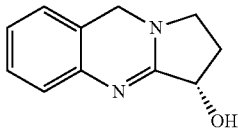

3 with a reducing agent in an organic or aqueous medium at a temperature ranging between 0° C. to 40° C. for a period ranging between 10 min to 1 hr to obtain aniline derivative of formula 4,

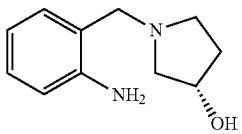

4 b. diazotisation of the aniline derivative of formula 4 and deamination of diazonium intermediate to obtain (S)-(−)-N-benzyl-3-hydroxypyrrolidine of formula 1,

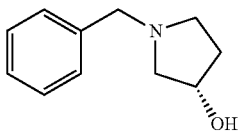

1 c. reacting (S)-(−)-N-benzyl-3-hydroxypyrrolidine of formula 1 with to reagent system selected from a group comprising triphenyl phoshine and diethyl azodicarboxylate (DEAD), and diisopropyl azodicarboxylate (DIAD), at a temperature ranging between 0° C. to 25° C. for period ranging between 1 hr to 16 hr followed by addition of an acid selected from a group of an organic acid consisting of formic acid, acetic acid, propionic acid. adjusting the pH in the range of 8-9 by addition of ammonia to obtain the intermediate compound of formula 5,

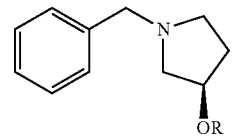

5

R=HCO,CH₃CO,CH₃CH₂CO,CH₃CH₂CH₂CO d. hydrolyzing the intermediate compound of formula 5 by reacting with a base at a temperature ranging between 0° C. to 25° C. for a period ranging between 1 hr to 3 hr to obtain the (R)-(+)-N-benzyl-3-hydroxypyrrolidine of formula 2 selected from a group consisting of lithium hydroxide, sodium hydroxide, and potassium hydroxide.

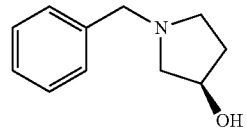

2

In an embodiment of the present invention wherein the reducing, agent may be selected from the hydride transfer reagents such as borohydrides, aluminum hydrides, boranes.

In another embodiment of the present invention wherein the reducing agent may be used in organic phase such as in methanol, aqueous methanol ethanol, aqueous ethanol, tetrahydrofuran, aqueous THF, dimethoxy ethane, diethyl ether, acetic acid and the like. In yet another embodiment of the present invention wherein the diazotization of the aniline intermediate of formula 4 is affected by using alkali metal nitrite or organic nitrite selected from a group consisting of sodium nitrite, potassium nitrite, amyl nitrite in presence of an acid catalyst.

In still another embodiment of the present invention wherein the acid catalyst is selected from an acid selected from sulphuric acid, hydrochloric acid, phosphoric acid, orthophosphoric acid, acetic acid, trifluoroacetic acid.

In an embodiment of the present invention wherein deamination of diazonium intermediate is effected using the acid catalyst wherein the catalyst is selected from a mineral acids such sulphuric, nitric acid, phosphoric acid, hydrochloric acid, hypophosphorus acid.

In a further embodiment of the present invention wherein the diazotization reaction is carried out at a temperature ranging between −10° to 50° C. preferably −5° C. to +10° C.

In an embodiment of the present invention wherein the isolation of the product (S)-(−)-N-benzyl-3-hydroxypyrrolidine of formula 1 is effected in basic pH preferably between 7-9, maintained by adding a base selected from a group consisting of ammonia, sodium hydroxide, potassium carbonate.

In an embodiment of the present invention wherein the purification of product is achieved by chromatography over alumina or silica gel.

BRIEF DESCRIPTION OF THE DRAWINGS

In the drawings, FIG. 1 illustrates various precursors to (R) and (S)-N-benzyl-3-hydroxypyrrolidines.

DETAILED DESCRIPTION OF THE INVENTION

The present invention relates to facile and highly efficient process for the preparation of optically pure (R) and (S)-N-benzyl-3-hydroxypyrrolidines. The process utilizes an alkaloid as the raw material which is easily isolated from a renewable plant source e.g. *Adhatoda vasica*, which grows in abundance, the process is simple, economical and can be upscaled for the commercial production of enantiomerically pure (S) and (R)-N-benzyl-3-hydroxypyrrolidines.

In this process the natural product vasicine in its enantiomerically pure crystalline form was used as a raw material. (S)-N-benzyl-3-hydroxypyrrolidine and (R)-N-benzyl-3-hydroxypyrrolidines represented by structure formulae 1 and 2 respectively are prepared using the following reaction steps—

1. Cleavage of C=N bond in alkaloid (−)-vasicine by using a suitable reducing agent.
2. Deamination of the intermediate aromatic amine to obtain (S)-N-benzyl-3-hydroxypyrrolidine.

3. Stereoinversion at position C-3 by Mitsunobu reaction to prepare second enantiomer (R)-N-benzyl-3-hydroxypyrrolidine The present invention relates to an efficient process for the preparation of enantiomerically pure N-benzyl-3-hydroxypyrrolidine using alkaloid (−)-vasicine as the raw material for its preparation. The process according to the present invention comprises of following steps.

1. Cleavage of an imine bond in vasicine of formula 3 by using a reducing agent to obtain (S)-(−)-N-(2-aminobenzyl)-3-hydroxy pyrrolidine intermediate of formula 4.
2. Deamination of (S)-(−)-N-(2-aminobenzyl)-3-hydroxypyrrolidine intermediate of formula 4 via diazotization and hydrodediazotisation to get (S)-(−) enantiomer of N-benzyl 3-hydroxy pyrrolidine of formula 1.
3. Stereoinversion (S)-(−)-N-benzyl-3-hydroxypyrrolidine of formula 1 to (R)-(+)-N-benzyl 3-hydroxypyrrolidine of formula 2 by Mitsunobu inversion reaction.

The natural alkaloid vasicine represented by the structure formula 3

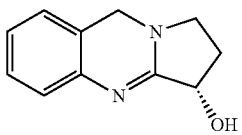

is used as a starting material is isolated from the plant *Adhatoda vasica* in its pure enantiomeric form. The plant is widely distributed in India and other parts of the globe. Yield of vasicine from the dry parts of the plant varies (0.5-2.5%) with seasonal changes and the climatic locations. The mp of the pure raw material vasicine used for the present invention obtained from *Adhatoda vasica* is 210° C. and its specific rotation value $[\alpha]_D$-233 (C, 2.6 CHCl$_3$).

In the first step according to the present invention, the cleavage of imine (C=N) bond in vasicine is effectively achieved through the addition a reducing agent in an aqueous or organic phase. The reducing agents such as hydride transfer agents selected from NaBH$_4$, Ca(BH$_4$)$_2$, LiBH$_4$, LiAlH$_4$, Zn(BH$_4$)$_2$, Alkyl boranes, diborane, 9-BBN, NaCNBH$_4$, DIBAH, etc., but more preferably borohydrides are used for the reductive cleavage at room temperature. The novel method of cleaving of imine (C=N) bond in vasicine has been developed first time by inventors of present invention. The solvent used in this method are selected from medium polar to polar solvents such as dichloro methane, ethyl acetate, carbon tetrachloride, methanol, ethanol, water, DMSO, acetic acid or their admixtures preferably aqueous medium at ambient temperature. After the completion of the reaction the C=N cleaved product (S)-N-(2-aminobenzyl)-3-hydroxypyrrolidine of structure formula 4

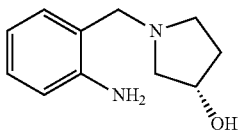

is extracted from the reaction mixture by organic solvents using a general method of isolation.

In the next step of the process, the intermediate (S)-N-(2-aminobenzyl)-3-hydroxypyrrolidine of structure formula 4 is converted to (S)-(−)-N-benzyl-3-hydroxypyrrolidine of formula 1

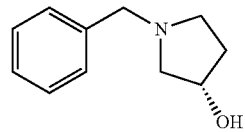

by diazotization, followed by addition of an acid such as orthophosphoric acid for hydrodediazotisation. The process of hydrodediazotisation involves the replacement of diazonium group by hydrogen, thus effecting the removal of primary amino group. The intermediate amine of structure formula 4 is first converted to diazonium salt by reacting it with alkali metal nitrites such as sodium nitrite, potassium nitrite or organic nitrite such as amyl nitrite, however, more preferably inorganic nitrite in an acidic medium. The acid used for effecting the diazotization reaction may be selected from mineral acid such as sulphuric acid, hydrochloric acid, phosphoric acid, orthophosphoric acid, acetic acid, trifluoroacetic acid and the like. The diazotization reaction is carried out at a temperature in the range −10° to +50° C. preferably at −5° C. to +10° C. The hydrodediazotisation reaction of the diazonium intermediate is indicated through a slow evolution of the nitrogen gas during the reaction. The desired product (S)-(−)-N-benzyl-3-hydroxypyrrolidine of formula 1 is extracted after basification of the reaction mixture by addition of ammonia or any other base to bring the pH of the solution between 7-9.

The product of formula 1 is extracted in an organic solvent, washed with water, desolvetized and finally purified by chromatography over alumina.

For the preparation of (R)-(+)-N-benzyl-3-hydroxypyrrolidine of formula 2 from (S)-(−)-N-benzyl-3-hydroxypyrrolidine of formula 1, the inversion of configuration of hydroxyl function at C-3 is effected by using Mitsunobu reaction. The Mitsunobu reaction is an important method employed for the inversion of stereochemistry in alcohols. The order of addition of reagents in Mitsunobu reaction is very important. According to the process of the present invention, triphenyl phosphine in tetrahydrofuran (THF) are cooled to 0° C.-10° C. And to above solution, diethyl azodicarboxylate (DEAD) or diisopropyl azodicarboxylate (DIAD) dissolved in terahydrofuran THF is added slowly. Finally (S)-alcohol of formula 1 is slowly added the above solution. The resulting reaction mixture is stirred for 20-30 minutes, followed by drop wise addition of an organic acid such as selected from acetic acid, formic acid, propionic acid and the like preferably acetic acid. The reaction mixture is continued to stir overnight at room temperature. After the completion of the reaction, the solution is acidified by adding a dilute mineral acid (5%) while maintaining the temperature 0° C.-10° C. The aqueous layer is separated from the organic layer. The pH of the aqueous portion was adjusted to 8 by adding ammonia or any other base and extracted with chloroform. The dried chloroform portion evaporated under reduced pressure to furnish inversion product (R)-(+)-N-benzyl-3-acyloxypyrrolidine of formula 5 in almost quantitative yields. For the preparation (R)-(+)-N-benzyl-3-hydroxypyrrolidine, the acylate of formula 5

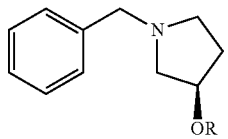

R=HCO,CH₃CO,CH₃CH₂CO,CH₃CH₂CH₂CO is dissolved in an organic solvent such as methanol, ethanol, tetrahydrofuran or their admixtures and thereafter hydrolysed in presence of an alkali such as sodium hydroxide, lithium hydroxide, potassium carbonate and the like. The hydrolysed product (R)-(+)-N-benzyl-3-hydroxypyrrolidine of formula 2

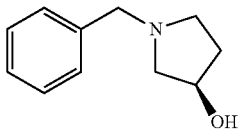

is isolated from the reaction mixture using a suitable organic solvent followed by removal of the solvent and purification of the crude product by chromatography over alumina.

The invention is described with reference to examples given below. These examples should not be construed as to restrict the scope of the present invention.

EXAMPLE-1

A. Preparation of (S)(−)-N-(2-Aminobenzyl)-3-Hydroxypyrrolidine of Structure Formula 4

Pure natural vasicine 10 g (0.05291 mol) $[\alpha]^{25}{}_D$-233 (C, 2.6 CHCl₃) of formula 3 was dissolved in 100 mL of methanol-water solution (1:1) in 250 mL of round bottom flask fitted with a stirrer. Sodium borohydride 5.87 g (0.15873 mol) was added in small portions to above solution at regular intervals at room temperature and stirring continued for another 10 hrs. The reaction proceeded through the formation of dihydro derivative of vasicine which eventually reduced completely via N—C bond cleavage. The reaction was quenched with ethyl acetate (10 mL) and product was extracted with chloroform (3×100 mL). The dried chloroform extract evaporated at reduced pressure on a thin film evaporator and chromatography over neutral alumina and elution with chloroform-metanol gave a semi-solid light yellow compound of formula 2 in 90% yield $[\alpha]^{25}{}_D$-199 (ee, 97%).

¹H NMR (CDCl₃, 200 MHz); δ 1.75 (m, 1H), 2.21 (m, 1H), 2.34 (m, 1H), 2.50 (bs, 1H), 2.60 (m, 1H), 2.89 (m, 1H), 3.71 (s, 2H), 4.31 (m, 1H), 6.68 (m, 2H), 7.10 (m, 2H).

B. Preparation of (S)(−)-N-Benzyl 3-Hydroxypyrrolidine of Formula 1 from Intermediate of Formula 4

Powdered sodium nitrite 7.4 g (0.105 moles) was added in small portions to 97% concentrate sulphuric acid (15 mL) with gentle stirring at −0° C. A solution of 5 g intermediate of formula 4 in 15 mL of 97% conc. sulphuric acid was added drop wise during stirring. The temperature of the reaction maintained below 5° C., and stirring was continued for 4-6 hr in an ice bath. The reaction mixture was then poured with vigorous stirring into a mixture of 15 g of (0.35 moles) of hypophosphoric acid and 150 g of ice. Considerable fuming occurred and the mixture was allowed to stand for several hours with occasional stirring and then overnight at room temperature. The pH of reaction mixture was adjusted to 8 by adding ammonia solution and extracted with chloroform (3×50 mL). After evaporation of the solvent and chromatography over alumina using dichloromethane:methanol (99:1), the product of formula 1 obtained in ~70% yield (3.22 g) $[\alpha]^{25}{}_D$-3.64 (c, 2.5 CHCl₃)(ee 95%).

¹H NMR (CDCl₃, 200 MHz); δ 1.75 (m, 1H), 2.21 (m, 1H), 2.34 (m, 1H), 2.50 (bs, 1H), 2.60 (m, 1H), 2.89 (m, 1H), 3.71 (s, 2H), 4.31 (m, 1H), 7.29 (s, 5H).

Example-2

A. Preparation of (S)(−)-N-Benzyl-3-Hydroxypyrrolidine of Structure Formula 1

A three necked flask (1 lit), equipped with a mechanical stirrer, thermometer and surrounded by an ice bath, is charged with pre-cooled mixture of 200 mL of concentrated sulfuric acid and 100 mL of water. Temperature of the stirring mixture is lowered to −5° C. and 7.4 g (0.108 mol) of sodium nitrite added in small portions over a period of 15 min. Cold 50% hypophosphorous acid (39 ml, 0.38 mol) is then added over a period of 10 min, while temperature maintained below −5° C. A solution of 5 g of intermediate 4 in 200 mL of glacial acetic acid is added to the stirring diazotization solution from a dropping funnel during the period of 1.5 hr. while the temperature is held at −5° C. during addition. Stirring of the slurry is continued for approximately 2 hr. and the temperature is allowed to rise gradually to 5° C. The loosely stopper flask is kept in a refrigerator for 36 hr. During this time nitrogen gas and some other oxides are evolved. The pH of reaction mixture was adjusted to 8 by adding ammonia and extracted with chloroform (3×50 mL). After usual processing and chromatography over alumina, the yield of the final product of formula 1 was 3.68 g (80%) $[\alpha]^{25}{}_D$-3.64 (c, 2.5 CHCl₃) (ee 95%).

¹H NMR (CDCl₃, 200 MHz); δ 1.75 (m, 1H), 2.21 (m, 1H), 2.34 (m, 1H), 2.50 (bs, 1H), 2.60 (m, 1H), 2.89 (m, 1H), 3.71 (s, 2H), 4.31 (m, 1H), 7.29 (s, 5H).

Example-3

Preparation of (S)(−)-N-Benzyl-3-Hydroxypyrrolidine from Intermediate of Formula 4

In a fume hood 10 M isoamyl nitrite in DMF (23 mL) is placed in a 100 mL round-bottomed flask containing a magnetic spin vane. A reflux condenser is placed on the clamped flask in a heated bath at 65° C. so as to maintain temperature of around 45° C. inside the flask. To the stirring solution, 5 g of intermediate 4 (0.026 moles) dissolved in a minimal amount of DMF (1 mL) is added dropwise over a period of 5 min. The evolution of nitrogen gas is immediate and continues until all of the substrate is added. After the gas evolution is completed (approximately 15 min), the reaction mixture is allowed to cool to room temperature. The pH of reaction mixture adjusted to 8 by adding ammonia and extracted with chloroform (3×50 mL). After processing and removal of the solvent, the yield of product of formula 1 was 1.475 g (80%) $[\alpha]^{25}{}_D$-3.60 (c, 2.5 CHCl₃) (ee 95%).

Example-4

Preparation of (S)(−)-N-Benzyl-3-Hydroxypyrrolidine of Formula 1

The intermediate 4, 5.75 g (0.03 moles) was dissolved of in 60 mL of rectified spirit and 15 mL of benzene in a 200 mL of two necked flask fitted with reflux condenser the second neck being closed with a stopper. Concentrated sulphuric acid (3.5 mL) was added dropwise of to the solution via the side-neck while gently swirling the liquid, followed by heating on a water bath until the clear solution. The flask is removed from the water bath, 6 g of powdered sodium nitrite is added in two equal portions via the side-neck; after each addition, replace the stopper and shake the flask vigorously; when the reaction subsided, add the second portion of nitrite. The heating continued on the water bath as long till the evolution of the gas ceased. The solution is cooled for 10 min in an ice bath. The pH of reaction mixture was adjusted to 8 by adding ammonia and extracted with chloroform (3×50 mL). After processing and removal of the solvent, the yield of product of formula 1 was 3.186 g (60%)$[\alpha]^{25}_D$-3.55 (c, 2.5 CHCl$_3$) (ee 93%).

Example-5

Preparation of (R)-(+)-N-Benzyl 3-Hydroxypyrrolidine of Formula 2

A(I): Preparation of Intermediate (R)-Ester of Formula 5

A stirred solution of triphenylphosphine (41.78 mmol) in dry THF (300 mL) was maintained at 0° C. under nitrogen atmosphere. Diisopropyl azodicarboxylate (DIAD) (7.0 mL, 35.17 mmol) was added drop wise to the resulting solution at the same temperature for 15 min. Where upon it became creamy white, (−)- alcohol of molecular formula 1 (6.71 gm in 25 mL THF) was added drop wise and stirring continued for another 20 min, prior to the addition of acetic acid 70 mmol in one portion. The resulting mixture was stirred for 16 hr at room temperature. The reaction mixture was acidified with 1:1 hydrochloric acid water, aqueous layer separated from organic layer and pH of aqueous layer was adjusted to 8 by adding ammonia followed by extracted with chloroform (3×60 mL). After processing and removal of the solvent, the yield of product of the intermediate ester was 80% (6.63 g).

A(II): Preparation of Intermediate (R)-Ester of Formula 5

A stirred solution of triphenylphosphine (41.78 mmol) in dry THF (300 mL) was maintained at 0° C. under nitrogen atmosphere. Diethyl azodicarboxylate (DEAD) (35.17 mmol) was added drop wise to the resulting solution at the same temperature for 15 min. Where upon it became creamy white, (−)- alcohol of molecular formula 1 (6.71 gm in 25 mL THF) was added drop wise and stirring continued for another 20 min, prior to the addition of acetic acid 70 mmol in one portion. The resulting mixture was stirred for 16 hr at room temperature. The reaction mixture was acidified with 1:1 hydrochloric acid water, aqueous layer separated from organic layer and pH of aqueous layer was adjusted to 8 by adding ammonia followed by extracted with chloroform (3×60 mL). After processing and removal of the solvent, the yield of product of the intermediate ester was 73% (6.049 g).

B(I). Hydrolysis of (R)-Ester of Formula 5 to Prepare Hydroxide (R)-(+)-N-Benzyl 3-Hydroxypyrrolidine of Formula 2

The intermediate ester of formula 5 prepared above without purification (0.3 mmol) was dissolved in a mixture (10 mL) of THF and methanol (3:1), and the aqueous solution of lithium hydroxide monohydrate (0.5 mmol, 1 mL) was added to it. The reaction mixture was stirred for 2 hr at 0° C. and then diluted with a saturated aqueous solution of ammonium chloride (20 ml); the resulting mixture was extracted with chloroform (3×60 mL). After processing and removal of the solvent and column chromatography over alumina, the yield of product of formula 2 was 96%, $[\alpha]^{25}_D$+3.53 (c, 2.5 CHCl$_3$) (ee, 93%).

B(II). Hydrolysis of (R)-Ester of Formula 5 to Prepare Hydroxide (R)-(+)-N-Benzyl 3-Hydroxypyrrolidine of Formula 2

The intermediate ester of formula 5 prepared above without purification (0.3 mmol) was dissolved in a mixture (10 mL) of THF and methanol (3:1), and the aqueous solution of potassium hydroxide (0.5 mmol, 1 mL) was added to it. The reaction mixture was stirred for 2 hr at 0° C. and then diluted with a saturated aqueous solution of ammonium chloride (20 ml); the resulting mixture was extracted with chloroform (3×60 mL). After processing and removal of the solvent and column chromatography over alumina, the yield of product of formula 2 was 80%, $[\alpha]^{25}_D$+3.53 (c, 2.5 CHCl$_3$) (ee, 93%).

B(III). Hydrolysis of (R)-Ester of Formula 5 to Prepare Hydroxide (R)-(+)-N-Benzyl 3-Hydroxypyrrolidine of Formula 2

The intermediate ester of formula 5 prepared above without purification (0.3 mmol) was dissolved in a mixture (10 mL) of THF and methanol (3:1), and the aqueous of solution Sodium hydroxide (0.5 mmol, 1 mL) was added to it. The reaction mixture was stirred for 2 hr at 0° C. and then diluted with a saturated aqueous solution of ammonium chloride (20 ml); the resulting mixture was extracted with chloroform (3×60 mL). After processing and removal of the solvent and column chromatography over alumina, the yield of product of formula 2 was 77%, $[\alpha]^{25}_D$+3.53 (c, 2.5 CHCl$_3$) (ee, 93%).

We claim:

1. A process for the preparation of optically active N-benzyl-3-hydroxypyrrolidine from (−)-vasicine comprising the steps:

(a) reacting (−)-vasicine of formula 3

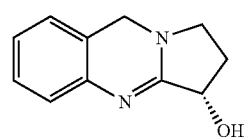

3

(b) with a reducing agent in an organic or aqueous medium at a temperature ranging between 0° C. to 40° C. for a period ranging between 10 min to 1 hr to obtain aniline derivative of formula 4,

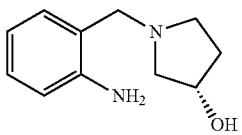

(c) diazotisation of the aniline derivative of formula 4 and deamination of diazonium intermediate to obtain (S)-(−)-N-benzyl-3-hydroxypyrrolidine of formula 1,

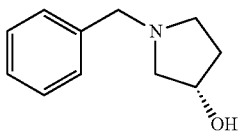

(d) reacting (S)-(−)-N-benzyl-3-hydroxypyrrolidine of formula 1 with a reagent system selected from a group comprising triphenyl phoshine, diethyl azodicarboxylate (DEAD), and diisopropyl azodicarboxylate (DIAD), at a temperature ranging between 0° C. to 25° C. for period ranging between 1 hr to 16 hr followed by addition of an acid selected from a group of an organic acid consisting of formic acid, acetic acid, and propionic acid and adjusting the pH in the range of 8-9 by addition of ammonia to obtain the intermediate compound of formula 5,

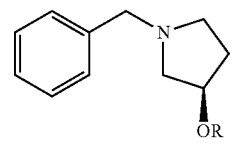

wherein R is selected from the group consisting of HCO, $CH_3CO$, $CH_3CH_2CO$, and $CH_3CH_2CH_2CO$; and (e) hydrolyzing the intermediate compound of formula 5 by reacting with a base at a temperature ranging between 0° C. to 25° C. for a period ranging between 1 hr to 3 hr to obtain the (R)-(+)-N-benzyl-3-hydroxypyrrolidine of formula 2 selected from a group consisting of lithium hydroxide, sodium hydroxide, and potassium hydroxide

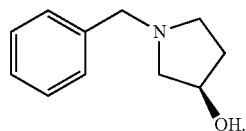

2. The process according to claim 1, wherein the reducing agent is a hydride transfer reagent selected from the group consisting of borohydrides, aluminum hydrides, and boranes.

3. The process according to claim 2, wherein the reducing agent is used in an organic phase selected from the group consisting of methanol, aqueous methanol ethanol, aqueous ethanol, tetrahydrofuran, aqueous THF, dimethoxy ethane, diethyl ether, and acetic acid.

4. The process according to claim 1, wherein the diazotization of the aniline derivative of formula 4 is effected by using alkali metal nitrite or organic nitrite selected from the group consisting of sodium nitrite, potassium nitrite, and amyl nitrite in presence of an acid catalyst.

5. The process according to claim 4, wherein the acid catalyst is an acid selected from the group consisting of sulphuric acid, hydrochloric acid, phosphoric acid, orthophosphoric acid, acetic acid, and trifluoroacetic acid.

6. The process according to claim 1, wherein deamination of diazonium intermediate is effected by using an acid catalyst wherein the acid catalyst is a mineral acid selected from the group consisting of sulphuric acid, nitric acid, phosphoric acid, hydrochloric acid, and hypophosphorus acid.

7. The process according to claim 4, wherein the diazotization reaction is carried out at a temperature ranging between −10° to 50° C.

8. The process according to claim 1, wherein the isolation of the product (S)-(−)-N-benzyl-3-hydroxypyrrolidine of formula 1 is effected in basic pH, maintained by adding a base selected from the group consisting of ammonia, sodium hydroxide, and potassium carbonate.

9. The process according to claim 1, further comprising the step of purifying the product, achieved by chromatography over alumina or silica gel.

10. The process according to claim 7, wherein the diazotisation reaction is carried out at a temperature ranging between −5° to 10° C.

11. The process according to claim 8, wherein the isolation of the product (S)-(−)-N-benzyl-3-hydroxypyrrolidine of formula 1 is effected in a basic pH of between 7 and 9.

* * * * *